United States Patent
Orbay et al.

(10) Patent No.: US 7,905,909 B2
(45) Date of Patent: *Mar. 15, 2011

(54) BONE STABILIZATION SYSTEM INCLUDING MULTI-DIRECTIONAL THREADED FIXATION ELEMENT

(75) Inventors: Jorge L. Orbay, Coral Gables, FL (US);
Alfredo Castaneda, Miami, FL (US);
Javier E. Castaneda, Miami, FL (US);
Robert Sixto, Jr., Miami, FL (US);
Edward Mebarak, Miami, FL (US)

(73) Assignee: Depuy Products, Inc., Warsaw, IN (US)

( * ) Notice: Subject to any disclaimer, the term of this patent is extended or adjusted under 35 U.S.C. 154(b) by 608 days.

This patent is subject to a terminal disclaimer.

(21) Appl. No.: 11/384,773

(22) Filed: Mar. 20, 2006

(65) Prior Publication Data

US 2007/0088360 A1    Apr. 19, 2007

Related U.S. Application Data

(63) Continuation-in-part of application No. 11/230,021, filed on Sep. 19, 2005, now Pat. No. 7,695,502.

(51) Int. Cl.
*A61B 17/80* (2006.01)
(52) U.S. Cl. .................. 606/291; 606/280
(58) Field of Classification Search .............. 606/69, 606/60, 280, 282, 286, 289–291
See application file for complete search history.

(56) References Cited

U.S. PATENT DOCUMENTS

| | | | |
|---|---|---|---|
| 388,000 A | 8/1888 | Rider | |
| 472,913 A | 4/1892 | Taylor | |
| 1,151,861 A | 8/1915 | Brumback | |
| 2,056,688 A | 10/1936 | Peterka et al. | |
| 2,500,370 A | 3/1950 | McKibbin | |
| 2,526,959 A | 10/1950 | Lorenzo | |
| 3,025,853 A | 3/1962 | Mason | |
| 3,236,141 A | 2/1966 | Smith | |

(Continued)

FOREIGN PATENT DOCUMENTS

CA    2174293 A    10/1997

(Continued)

OTHER PUBLICATIONS

Summary of Safety and Effectiveness Information (510(k) Summary), Synthes USA, Jul. 29, 1998.

(Continued)

*Primary Examiner* — Thomas C Barrett
*Assistant Examiner* — Nicholas Woodall
(74) *Attorney, Agent, or Firm* — Gordon & Jacobson, PC

(57) ABSTRACT

A bone fixation system includes a plate and a set of fixation locking screws. The plate defines a set of locking screw holes each having an internal thread. Each respective locking screw has a head with an external structure that is adapted to self-tap into the internal thread of a given locking screw hole to secure the respective first-type fixation locking screw at an surgeon-directed angle relative to the plate. This angle is defined during forcible insertion and rotation of the respective locking screw into the given screw hole. The system may also include unidirectional locking screws. In a preferred embodiment the plate and first-type of screw are made of different metals, with the plate made of titanium alloy and the screw made of cobalt chrome alloy.

8 Claims, 12 Drawing Sheets

U.S. PATENT DOCUMENTS

| | | |
|---|---|---|
| 3,645,161 A | 2/1972 | Wesker |
| 3,709,218 A | 1/1973 | Halloran |
| 3,717,146 A | 2/1973 | Halloran |
| 3,741,205 A | 6/1973 | Markoff et al. |
| 3,842,825 A | 10/1974 | Wagner |
| 3,939,498 A | 2/1976 | Lee et al. |
| RE28,841 E | 6/1976 | Allgower et al. |
| 4,011,863 A | 3/1977 | Zickel |
| 4,119,092 A | 10/1978 | Gil |
| 4,135,507 A | 1/1979 | Harris |
| 4,153,953 A | 5/1979 | Grobbelaar |
| 4,169,470 A | 10/1979 | Ender et al. |
| 4,172,452 A | 10/1979 | Forte et al. |
| 4,408,601 A | 10/1983 | Wenk |
| 4,467,793 A | 8/1984 | Ender |
| 4,473,069 A | 9/1984 | Kolmert |
| 4,483,335 A | 11/1984 | Tornier |
| 4,484,570 A | 11/1984 | Sutter et al. |
| 4,488,543 A | 12/1984 | Tornier |
| 4,493,317 A | 1/1985 | Klaue |
| 4,506,662 A | 3/1985 | Anapliotis |
| 4,565,193 A | 1/1986 | Streli |
| 4,651,724 A | 3/1987 | Berentey et al. |
| 4,712,541 A | 12/1987 | Harder et al. |
| 4,733,654 A | 3/1988 | Marino |
| 4,776,330 A | 10/1988 | Chapman et al. |
| 4,794,919 A | 1/1989 | Nilsson |
| 4,800,874 A | 1/1989 | David et al. |
| 4,867,144 A | 9/1989 | Kara et al. |
| 4,905,680 A | 3/1990 | Tunc |
| 4,915,092 A | 4/1990 | Firica et al. |
| 4,923,471 A | 5/1990 | Morgan |
| 4,955,886 A | 9/1990 | Pawluk |
| 5,006,120 A | 4/1991 | Carter |
| 5,013,313 A | 5/1991 | Surer |
| 5,013,314 A | 5/1991 | Firica et al. |
| 5,015,248 A | 5/1991 | Burstein et al. |
| 5,035,697 A | 7/1991 | Frigg |
| 5,041,113 A | 8/1991 | Biedermann et al. |
| 5,057,110 A | 10/1991 | Kranz et al. |
| 5,085,660 A | 2/1992 | Lin |
| 5,127,912 A | 7/1992 | Ray et al. |
| 5,147,361 A * | 9/1992 | Ojima et al. ................. 606/70 |
| 5,151,103 A | 9/1992 | Tepic et al. |
| 5,190,544 A | 3/1993 | Chapman et al. |
| 5,197,966 A | 3/1993 | Sommerkamp |
| 5,201,733 A | 4/1993 | Etheredge, III |
| 5,275,601 A | 1/1994 | Gogolewski et al. |
| 5,304,180 A | 4/1994 | Slocum |
| 5,306,275 A | 4/1994 | Bryan |
| 5,352,228 A | 10/1994 | Kummer et al. |
| 5,352,229 A | 10/1994 | Goble et al. |
| 5,356,253 A | 10/1994 | Whitesell |
| 5,356,410 A | 10/1994 | Pennig |
| 5,364,399 A | 11/1994 | Lowery et al. |
| 5,382,248 A | 1/1995 | Jacobson et al. |
| 5,429,641 A | 7/1995 | Gotfried |
| 5,437,667 A | 8/1995 | Papierski et al. |
| 5,458,654 A | 10/1995 | Tepic |
| 5,470,333 A | 11/1995 | Ray |
| 5,472,444 A | 12/1995 | Huebner et al. |
| 5,484,438 A | 1/1996 | Pennig |
| 5,486,176 A | 1/1996 | Hildebrand et al. |
| 5,520,690 A | 5/1996 | Errico et al. |
| 5,527,311 A | 6/1996 | Procter et al. |
| 5,531,745 A | 7/1996 | Ray |
| 5,531,746 A | 7/1996 | Errico et al. |
| 5,536,127 A | 7/1996 | Pennig |
| 5,549,612 A | 8/1996 | Yapp et al. |
| 5,558,674 A | 9/1996 | Heggeness et al. |
| 5,578,035 A | 11/1996 | Lin |
| 5,586,985 A | 12/1996 | Putnam et al. |
| 5,591,168 A | 1/1997 | Judet et al. |
| 5,601,553 A * | 2/1997 | Trebing et al. ................. 606/61 |
| 5,603,715 A | 2/1997 | Kessler |
| 5,607,426 A | 3/1997 | Ralph et al. |
| 5,607,428 A | 3/1997 | Lin |
| 5,662,655 A | 9/1997 | Laboureau et al. |
| 5,665,086 A | 9/1997 | Itoman et al. |
| 5,665,087 A | 9/1997 | Huebner |
| 5,665,089 A | 9/1997 | Dall et al. |
| 5,669,915 A | 9/1997 | Caspar et al. |
| 5,676,667 A | 10/1997 | Hausman |
| 5,690,631 A | 11/1997 | Duncan et al. |
| 5,709,682 A | 1/1998 | Medoff |
| 5,709,686 A | 1/1998 | Talos et al. |
| 5,718,705 A | 2/1998 | Sammarco |
| 5,728,099 A | 3/1998 | Tellman et al. |
| 5,733,287 A | 3/1998 | Tepic et al. |
| 5,749,872 A | 5/1998 | Kyle et al. |
| 5,766,174 A | 6/1998 | Perry |
| 5,772,662 A | 6/1998 | Chapman et al. |
| 5,776,194 A | 7/1998 | Mikol et al. |
| 5,785,711 A | 7/1998 | Errico et al. |
| 5,807,396 A | 9/1998 | Raveh |
| 5,851,207 A | 12/1998 | Cesarone |
| 5,853,413 A | 12/1998 | Carter et al. |
| 5,879,350 A | 3/1999 | Sherman |
| 5,931,839 A | 8/1999 | Medoff |
| 5,935,128 A | 8/1999 | Carter et al. |
| 5,938,664 A | 8/1999 | Winquist et al. |
| 5,941,878 A | 8/1999 | Medoff |
| 5,951,557 A | 9/1999 | Luter |
| 5,954,722 A | 9/1999 | Bono |
| 5,964,763 A | 10/1999 | Incavo |
| 5,967,046 A | 10/1999 | Muller |
| 5,968,046 A | 10/1999 | Castleman |
| 5,968,047 A | 10/1999 | Reed |
| 5,984,925 A | 11/1999 | Apgar |
| 5,989,254 A | 11/1999 | Katz |
| 6,007,535 A | 12/1999 | Rayhack et al. |
| 6,010,503 A | 1/2000 | Richelsoph |
| 6,010,505 A | 1/2000 | Asche et al. |
| 6,022,350 A | 2/2000 | Ganem |
| 6,030,389 A | 2/2000 | Wagner et al. |
| 6,053,917 A | 4/2000 | Sherman |
| 6,096,040 A | 8/2000 | Esser |
| 6,123,709 A | 9/2000 | Jones |
| 6,129,730 A | 10/2000 | Bono et al. |
| 6,139,550 A | 10/2000 | Michelson |
| 6,146,384 A | 11/2000 | Lee et al. |
| 6,152,927 A | 11/2000 | Farris et al. |
| 6,183,475 B1 | 2/2001 | Lester et al. |
| 6,193,721 B1 | 2/2001 | Michelson |
| 6,197,028 B1 | 3/2001 | Ray et al. |
| 6,206,881 B1 | 3/2001 | Frigg et al. |
| 6,221,073 B1 | 4/2001 | Weiss et al. |
| D443,060 S | 5/2001 | Benirschke et al. |
| 6,228,085 B1 | 5/2001 | Theken et al. |
| 6,228,285 B1 | 5/2001 | Wang et al. |
| 6,231,576 B1 | 5/2001 | Frigg et al. |
| 6,235,033 B1 | 5/2001 | Brace et al. |
| 6,235,034 B1 | 5/2001 | Bray |
| 6,238,395 B1 | 5/2001 | Bonutti |
| 6,241,736 B1 | 6/2001 | Sater et al. |
| 6,248,109 B1 | 6/2001 | Stoffella |
| 6,258,089 B1 | 7/2001 | Campbell et al. |
| 6,270,499 B1 | 8/2001 | Leu et al. |
| 6,283,969 B1 | 9/2001 | Grusin et al. |
| 6,290,703 B1 | 9/2001 | Ganem |
| 6,296,642 B1 | 10/2001 | Morrison et al. |
| 6,322,562 B1 | 11/2001 | Wolter |
| 6,355,041 B1 | 3/2002 | Martin |
| 6,355,043 B1 | 3/2002 | Adam |
| 6,358,250 B1 | 3/2002 | Orbay |
| 6,364,882 B1 | 4/2002 | Orbay |
| 6,379,359 B1 | 4/2002 | Dahners |
| 6,383,186 B1 | 5/2002 | Michelson |
| 6,409,768 B1 | 6/2002 | Tepic et al. |
| 6,440,135 B2 | 8/2002 | Orbay et al. |
| 6,454,769 B2 | 9/2002 | Wagner et al. |
| 6,454,770 B1 | 9/2002 | Klaue |
| 6,458,133 B1 | 10/2002 | Lin |
| 6,468,278 B1 | 10/2002 | Muckter |
| 6,508,819 B1 | 1/2003 | Orbay |
| 6,527,775 B1 | 3/2003 | Warburton |
| 6,540,748 B2 | 4/2003 | Lombardo |

| | | |
|---|---|---|
| 6,585,738 B1 | 7/2003 | Mangione et al. |
| 6,595,993 B2 | 7/2003 | Donno et al. |
| 6,599,290 B2 | 7/2003 | Bailey et al. |
| 6,602,255 B1 | 8/2003 | Campbell et al. |
| 6,623,486 B1 * | 9/2003 | Weaver et al. .......... 606/69 |
| 6,626,908 B2 | 9/2003 | Cooper et al. |
| 6,645,212 B2 | 11/2003 | Goldhahn et al. |
| 6,669,700 B1 | 12/2003 | Farris et al. |
| 6,679,883 B2 | 1/2004 | Hawkes et al. |
| 6,692,503 B2 | 2/2004 | Foley |
| 6,706,046 B2 | 3/2004 | Orbay et al. |
| 6,712,820 B2 | 3/2004 | Orbay |
| 6,719,758 B2 | 4/2004 | Beger et al. |
| 6,730,090 B2 | 5/2004 | Orbay et al. |
| 6,730,091 B1 | 5/2004 | Pfefferle et al. |
| 6,755,831 B2 | 6/2004 | Putnam |
| 6,761,719 B2 | 7/2004 | Justis et al. |
| 6,767,351 B2 | 7/2004 | Orbay et al. |
| 6,780,186 B2 | 8/2004 | Errico et al. |
| 6,866,665 B2 | 3/2005 | Orbay |
| 6,926,720 B2 | 8/2005 | Castaneda |
| 6,955,677 B2 | 10/2005 | Dahners |
| 6,960,211 B1 | 11/2005 | Pfefferle et al. |
| 6,974,461 B1 | 12/2005 | Wolter |
| 7,063,702 B2 | 6/2006 | Michelson |
| 7,090,676 B2 | 8/2006 | Huebner et al. |
| 7,128,744 B2 | 10/2006 | Weaver et al. |
| 7,153,309 B2 | 12/2006 | Huebner et al. |
| 7,179,260 B2 | 2/2007 | Gerlach et al. |
| 7,273,481 B2 | 9/2007 | Lombardo et al. |
| 7,326,014 B2 * | 2/2008 | Levey et al. .......... 411/308 |
| 2001/0001119 A1 | 5/2001 | Lombardo |
| 2001/0011172 A1 | 8/2001 | Orbay et al. |
| 2001/0021851 A1 | 9/2001 | Eberlein et al. |
| 2002/0032446 A1 | 3/2002 | Orbay |
| 2002/0045901 A1 | 4/2002 | Wagner et al. |
| 2002/0049445 A1 | 4/2002 | Hall, IV et al. |
| 2002/0058939 A1 | 5/2002 | Wagner et al. |
| 2002/0058940 A1 | 5/2002 | Frigg et al. |
| 2002/0058941 A1 | 5/2002 | Clark et al. |
| 2002/0111629 A1 | 8/2002 | Phillips |
| 2002/0128654 A1 | 9/2002 | Steger et al. |
| 2002/0143341 A1 | 10/2002 | Biedermann et al. |
| 2002/0147452 A1 | 10/2002 | Medoff et al. |
| 2002/0151899 A1 | 10/2002 | Bailey et al. |
| 2002/0156474 A1 | 10/2002 | Wack et al. |
| 2003/0036758 A1 | 2/2003 | Frigg et al. |
| 2003/0045880 A1 | 3/2003 | Michelson |
| 2003/0078583 A1 | 4/2003 | Biedermann et al. |
| 2003/0083661 A1 | 5/2003 | Orbay et al. |
| 2003/0105461 A1 | 6/2003 | Putnam |
| 2003/0135212 A1 | 7/2003 | Chow |
| 2003/0153919 A1 | 8/2003 | Harris |
| 2003/0216735 A1 | 11/2003 | Altarac et al. |
| 2004/0030339 A1 * | 2/2004 | Wack et al. .......... 606/69 |
| 2004/0059334 A1 | 3/2004 | Weaver et al. |
| 2004/0059335 A1 | 3/2004 | Weaver et al. |
| 2004/0068319 A1 | 4/2004 | Cordaro |
| 2004/0073218 A1 | 4/2004 | Dahners |
| 2004/0097934 A1 | 5/2004 | Farris et al. |
| 2004/0102778 A1 | 5/2004 | Huebner et al. |
| 2004/0111090 A1 | 6/2004 | Dahners |
| 2004/0193155 A1 | 9/2004 | Castaneda |
| 2004/0193163 A1 | 9/2004 | Orbay |
| 2004/0204712 A1 | 10/2004 | Kolb et al. |
| 2004/0210220 A1 | 10/2004 | Tornier |
| 2004/0260291 A1 | 12/2004 | Jensen |
| 2004/0267261 A1 | 12/2004 | Derouet |
| 2005/0004574 A1 | 1/2005 | Muckter |
| 2005/0010226 A1 * | 1/2005 | Grady et al. .......... 606/69 |
| 2005/0049594 A1 | 3/2005 | Wack et al. |
| 2005/0080421 A1 | 4/2005 | Weaver et al. |
| 2005/0131413 A1 | 6/2005 | O'Driscoll et al. |
| 2005/0154392 A1 | 7/2005 | Medoff et al. |
| 2005/0165400 A1 | 7/2005 | Fernandez |
| 2005/0187551 A1 | 8/2005 | Orbay et al. |
| 2005/0261688 A1 | 11/2005 | Grady, Jr. et al. |
| 2006/0004462 A1 | 1/2006 | Gupta |
| 2006/0009771 A1 | 1/2006 | Orbay |
| 2006/0015101 A1 | 1/2006 | Warburton et al. |
| 2006/0149265 A1 | 7/2006 | James et al. |
| 2006/0161158 A1 | 7/2006 | Orbay et al. |

FOREIGN PATENT DOCUMENTS

| | | |
|---|---|---|
| CH | 675 531 | 10/1990 |
| CN | 1379642 A | 11/2002 |
| DE | 33 01 298 | 2/1984 |
| DE | 40 04 941 | 8/1990 |
| DE | 195 42 116 A | 5/1997 |
| DE | 196 29 011 | 1/1998 |
| DE | 93 21 544 U1 | 9/1999 |
| DE | 43 43 117 C2 | 11/1999 |
| DE | 10115014.8 A1 | 3/2001 |
| DE | 20200705 | 3/2002 |
| EP | 0 451 427 A1 | 5/1990 |
| EP | 0486762 | 5/1992 |
| EP | 0689800 | 1/1996 |
| EP | 1250892 | 10/2002 |
| EP | 1423057 B1 | 12/2006 |
| EP | 1654994 B1 | 4/2008 |
| FR | 2233973 | 1/1975 |
| FR | 2405062 | 5/1979 |
| FR | 2855391 | 12/2004 |
| JP | 7-10734 | 3/1995 |
| JP | 11047170 | 2/1999 |
| WO | WO 97/47251 | 12/1997 |
| WO | WO 00/04836 | 2/2000 |
| WO | WO 00/36984 | 6/2000 |
| WO | WO00/66011 | 11/2000 |
| WO | WO01/12081 | 2/2001 |
| WO | WO 01/19267 A | 3/2001 |
| WO | WO01/56452 | 8/2001 |
| WO | WO 2004/032751 | 4/2004 |
| WO | WO 2004/096067 | 11/2004 |
| WO | WO2005044121 A1 | 5/2005 |

OTHER PUBLICATIONS

"Advances in distal Radius Fracture Management (D)", transcript of American Academy of Orthopaedic Surgeons 2001 Conf.; pp. 134-151, Feb. 28, 2001 including Article by Matthew D. Putnam MD, "Repair and Rehabilitation of Distal Fractures: The Role of Subchondral Fixation" at pp. 144-147.

"SCS.TM./D Distal Radius Plate System: Dorsal", Avanta 1997.

"SCS.TM./V Distal Radius Plate: Volar", Avanta 1998.

"Summary of Safety and Effectiveness Information"; Synthes.RTM.; Jul. 29, 1998.

"The Distal Radius Plate Instrument and Implant Set", Technique Guide, SYNTHES.RTM., Paoli, PA 1995.

"The Titanium Distal Radius Plate", Technique Guide, SYNTHES. RTM., Paoli, PA, 1995.

Moftakhar, Roham, M.D. and Trost, Gregory R., M.D., "Anterior Cervical Plates: A Historical Perspective", Jan. 2004, pp. 1-5.

Polyaxial and Monoaxial Spinal Screws, XIA.TM. Spinal System, www.osteonics.com/osteonics/spine/xia2.html, Jun. 25, 2002.

Putnam, D. M.D., "Repair and Rehabilitation of Distal Fractures: The Role of Ssubchondral Fixation" at pp. 144-147.

Nelson, "Volar Plating with Anatomic Placement and Fixed-Angle Screws," Quick Reference Guide for Contours VPS Volar Plate System by Orthofix, May 2005, www.orthofix.com.

"SMARTLock Locking Screw Technology," Stryker Corporation, website description, 2004, www.stryker.com.

"Universal Distal Radius System," Stryker Corporation, website description, 2004, www. stryker.com.

"Numelock II Polyaxial Locking System," Stryker Corporation, brochure.

"Volar Peg Plate Insertion Technique," Trimed, Inc., brochure.

"VAL Plate (Volar Angle Locking) for Distal Radius Fractures," US Implants, brochure.

"Volar Radius Plate with Angular Stability," I.T.S. (Implant Technology Systems), 510(k) Summary of Safety and Effectiveness, Feb. 6, 2004.

"Volare Winkelstabile Radiusplatte," I.T.S. (Implant Technology Systems) Spectromed, brochure, 2005, Austria.

* cited by examiner

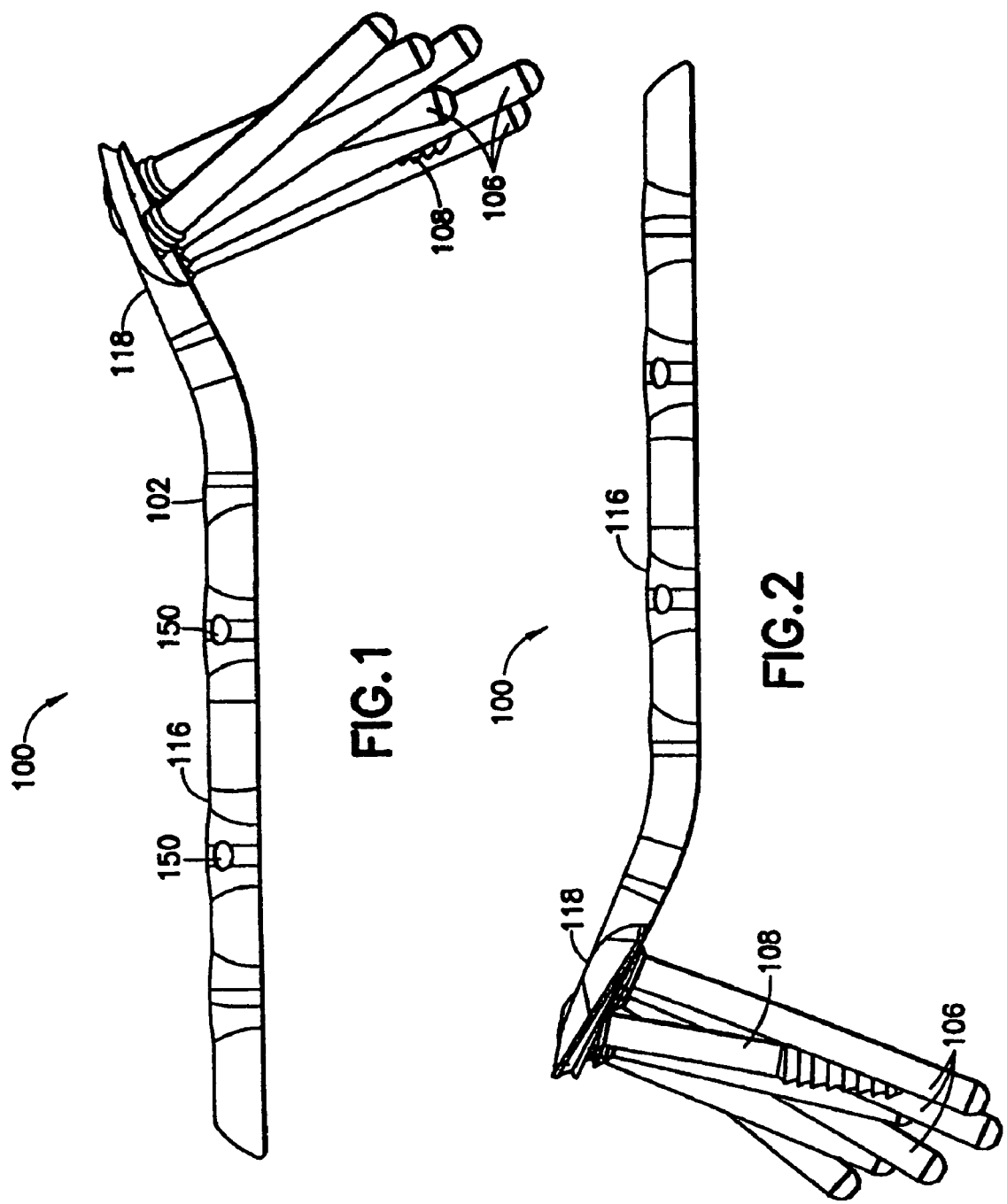

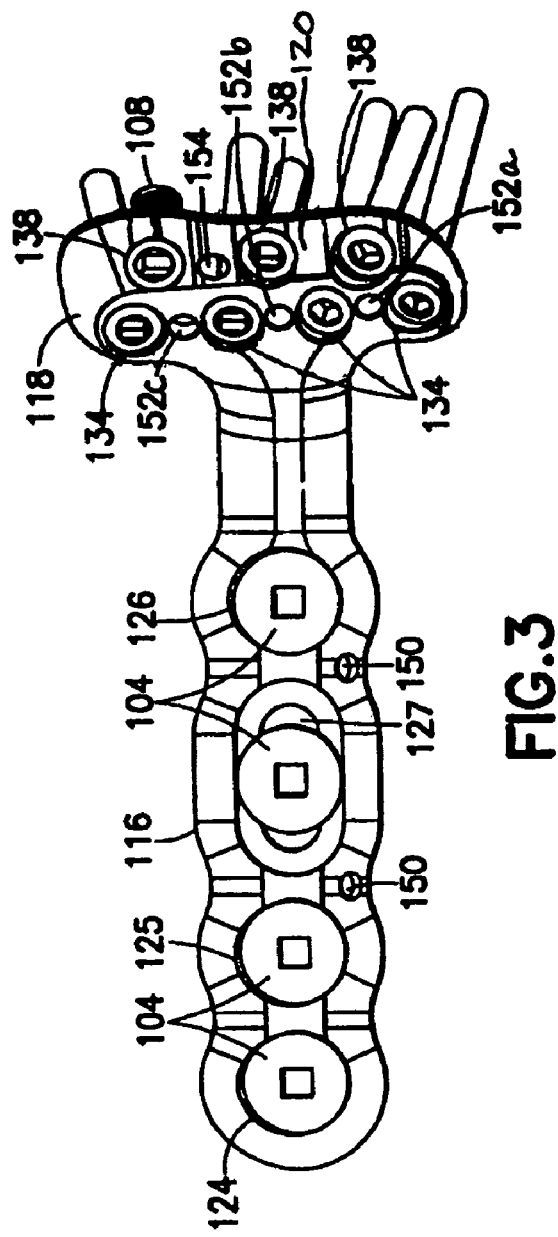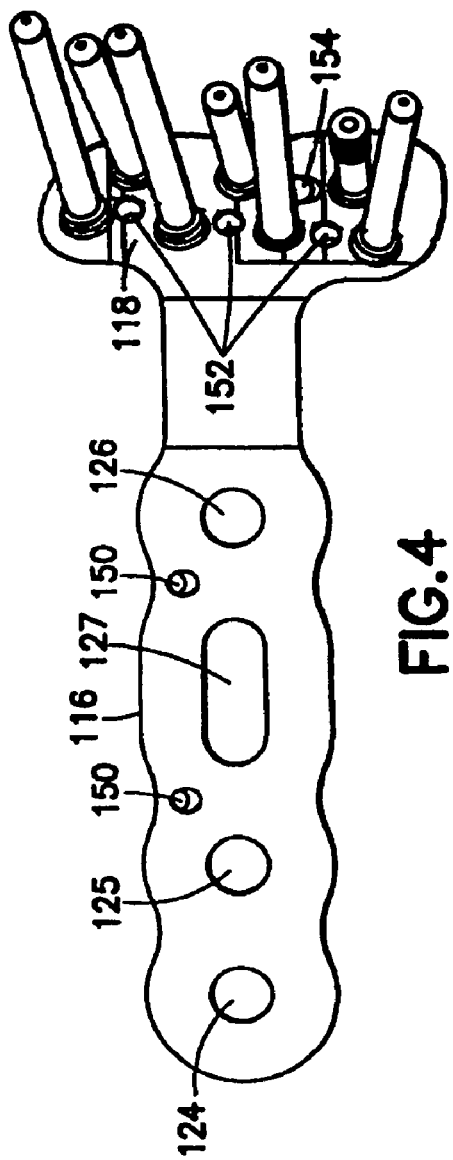

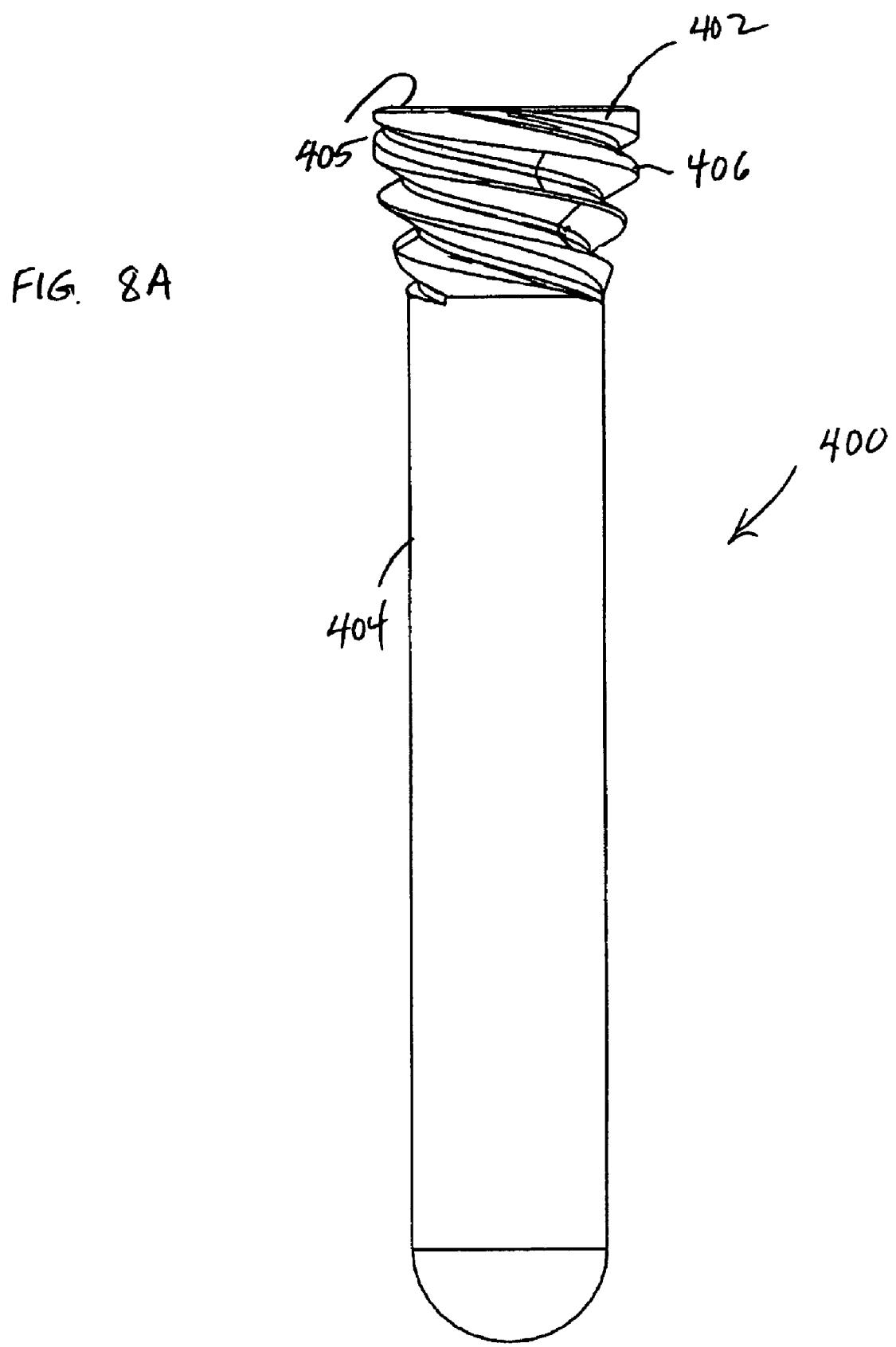

BONE STABILIZATION SYSTEM INCLUDING MULTI-DIRECTIONAL THREADED FIXATION ELEMENT

RELATED APPLICATIONS

This application is a continuation-in-part of U.S. Ser. No. 11/230,021, filed Sep. 19, 2005, which issued on Apr. 13, 2010, as U.S. Pat. No. 7,695,502, and which is hereby incorporated by reference herein in its entirety.

BACKGROUND OF THE INVENTION

1. Field of the Invention

This invention relates broadly to surgery. More particularly, this invention relates to a bone fixation systems including plates and locking screws.

2. State of the Art

Fracture to the metaphyseal portion of a long bone can be difficult to treat. Improper treatment can result in deformity and long-term discomfort.

By way of example, a Colles' fracture is a fracture resulting from compressive forces being placed on the distal radius, and which causes backward or dorsal displacement of the distal fragment and radial deviation of the hand at the wrist. Often, a Colles' fracture will result in multiple bone fragments which are movable and out of alignment relative to each other. If not properly treated, such fractures may result in permanent wrist deformity and limited articulation of the wrist. It is therefore important to align the fracture and fixate the bones relative to each other so that proper healing may occur.

Alignment and fixation of a metaphyseal fracture (occurring at the extremity of a shaft of a long bone) are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic. Plating utilizes a stabilizing metal plate that is typically placed against the dorsal side of a bone. Fixators extend from the plate into holes drilled in bone fragments are used to secure the fragments to the plate and thereby provide stabilized fixation of the fragments.

Commercially available are plates which use one of two types of fixators: i) unidirectional fixed angle locking screws (both smooth shaft screws and threaded shaft screws) that are fixed in a predetermined orientation relative to the plate with the head of the screws threadably engaging threaded holes in the plate, and ii) surgeon-directed or omnidirectional "locking" screws that can be fixed to the plate at any angle within a range of angles relative to the plate. Surgeon-directed locking screws are exemplified in SMARTLock™ screw system from Stryker Corporation, the Volar Bearing Plate™ from Trimed Inc., the VAL™ (volar angle locking) plate from US Implants, and the Viper™ plate with VALT™ (variable angle locking technology) from KMI Inc. The surgeon-directed "locking" screws require special structure and dedicated screw holes. All available plates with surgeon-directed locking screws have the hole axes for the screws all in a parallel orientation, and generally normal to the bone contacting surface of the plate. As the angle at which any surgeon-directed locking screw can be directed is limited relative to the hole axis (generally ±15°), the range of angles through which the screws can be inserted is greatly limited. As such, such systems often suffer from an inability to properly approach the desired anatomical structure with a fixator.

In addition, some plates permit the use of, or only use, non-locking screws in which there is no direct engagement between the head of the screw and the plate, but the screw shaft engages the bone and the plate and bone are held and relationship via compression created by driving the screw. Thus, in treating a particular bone fracture, an orthopedic surgeon is required to select one of these types of plate systems and the appropriate type of screws.

It is believed that a fixed angle locking screw, as opposed to a non-locking screw, provides advantage over the non-locking screw in that increased stability to the fracture is provided. In addition, compression which may be disadvantageous for many fractures is avoided.

There may be instances where improved bone stabilization and fixation can be accomplished utilizing both unidirectional and surgeon-directed locking screws. These features would allow the surgeon to better tailor the application of the plate system to the specific nature of the bone fracture suffered by the individual patient. However, no available system provides such capability.

SUMMARY OF THE INVENTION

It is therefore an object of the invention to provide a bone fixation system with a plate the supports both unidirectional and surgeon-directed fixation of the screws relative to the plate.

It is another object of the invention to provide a bone fixation system that provides the surgeon with flexibility, ease of use, and operational efficiency such that a screw hole can be used with both unidirectional and surgeon-directed screws.

It is also an object of the invention to provide a bone fixation system that is inexpensive to manufacture and requires minimal modification or reconfiguration of the plate in order to support both unidirectional and surgeon-directed fixation.

It is an additional object of the invention to provide a bone fixation systems suitable for stabilization of distal radius fractures as well as for other fractures.

In accord with these and other objects, which will be discussed in detail below, a bone fixation system includes a substantially rigid plate defining a set of threaded holes, wherein one or more of the threaded holes may be obliquely oriented relative to each other. The system also includes a first set of at least one surgeon-directed screw which can be fixed to the plate, and optionally a second set of at least one unidirectional fixed angle locking screw having a threaded head adapted to threadably engage with the threaded hole in a conventional manner. Each respective screw of the first set has a head with an external structure that is adapted to self-tap into the internal thread of a given hole to secure the respective screw at an arbitrary surgeon selected angle within a range of permissible angles relative to the plate. This angle is defined during forcible insertion and rotation of the screw into the given hole. Thus, the use of self-tapping locking screws permits the surgeon to modify the angle of approach of a fixed angle screw relative to the respective axes of screw holes which are already obliquely oriented relative to each other.

According to one embodiment, the self-tapping external structure of the head of each surgeon-directed screw of the first set is realized by a reverse-hand external thread, which may have a conical or spherical profile.

According to other embodiments, the self-tapping external structure of the head of each surgeon-directed screw of the first set is realized by an external thread that runs in the same direction as the internal threads of the threaded holes. In an embodiment, such external and internal threads are of significantly different pitch from each other. In another embodiment, the external threads are constructed of a harder material than the internal threads and also preferably are of a larger angle. The heads of each of these screws may have a conical or spherical profile.

According to another embodiment, the self-tapping external structure of the head of each surgeon-directed screw of the first set is realized by a set of external ridges and external grooves that are radially spaced apart from one another about the outer circumference of the head of the screw and that extend in vertical directions substantially parallel to the central axis of the screw. The ridges may a have constant width (or possibly a narrowing width) as they extend downward along the outer surface of the head of the screw.

Additional objects and advantages of the invention will become apparent to those skilled in the art upon reference to the detailed description taken in conjunction with the provided figures.

BRIEF DESCRIPTION OF THE DRAWINGS

FIG. 1 is a radial side elevation of a right-hand volar plate according to the invention, shown with locking screws coupled thereto;

FIG. 2 is an ulnar side elevation of a right-hand volar plate according to the invention, shown with locking screw coupled thereto;

FIG. 3 is top view of a right-hand volar plate according to the invention, shown with locking screws and cortical screws;

FIG. 4 is bottom view of a right-hand volar plate according to the invention, shown with locking screws coupled thereto;

FIG. 8A is a side view of a surgeon directed locking screw in accordance with the present invention.

DETAILED DESCRIPTION OF THE PREFERRED EMBODIMENTS

Figure 5:
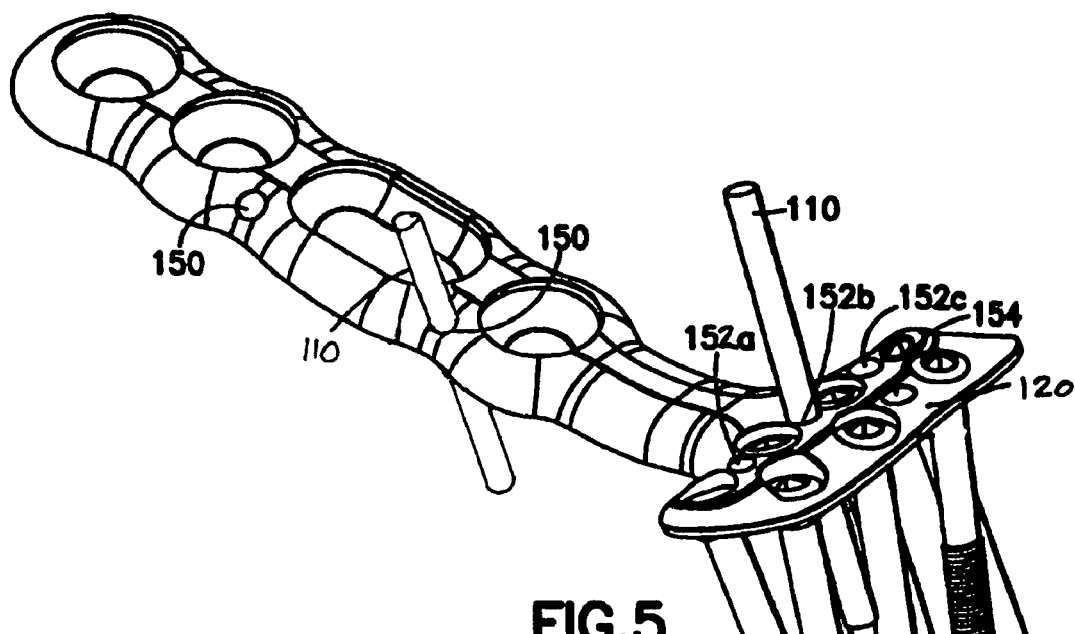
FIG. 5 is a perspective view of a right-hand volar plate according to the invention, shown with locking screws coupled thereto and K-wires extending through body portion alignment holes and through proximal head alignment holes.
Figure 6:
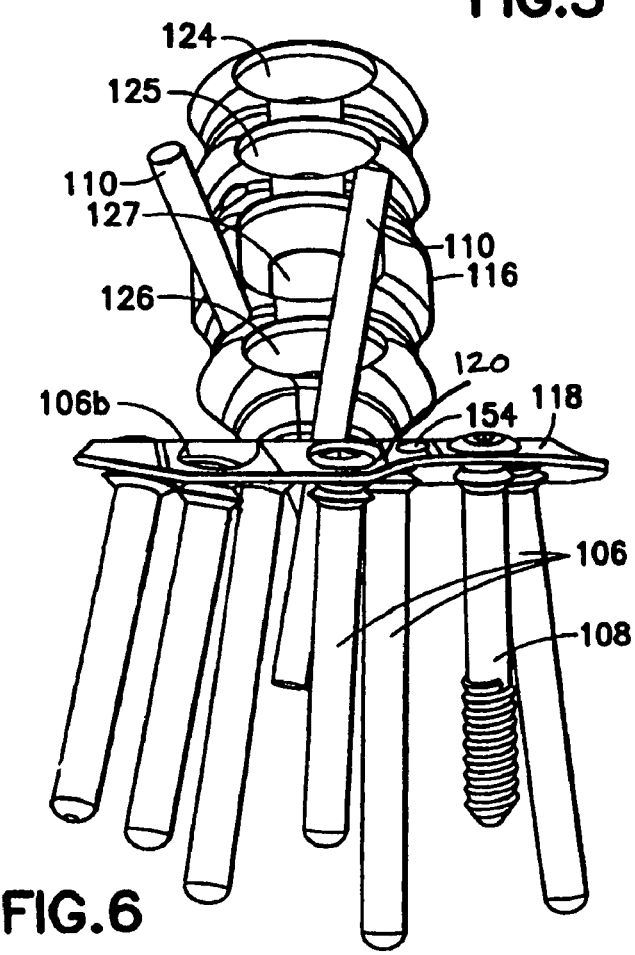
FIG. 6 is a front end view of a right-hand volar plate according to the invention, shown with locking screws coupled thereto and K-wires extending through body portion alignment holes and proximal head alignment holes.

Turning now to FIGS. 1 through 6, a fracture fixation system 100 according to the invention is shown. The system 100 shown and described is particularly adapted for aligning and stabilizing multiple bone fragments in a dorsally displaced distal radius fracture (or Colles' fracture), but the invention as described below is applicable to other surgical orthopedic bone stabilization systems for use in the treatment of this and other fractures.

The system 100 generally includes a substantially rigid T-shaped plate 102 for distal radius fractures, commonly called a volar plate, which is preferably made from a titanium alloy, such as Ti-6Al-4V. The plate includes a body 116 and a head 118. The system 100 also includes bone screws 104 (FIG. 3), a set of unidirectional locking screws 106, 108, and a set of surgeon-directed omnidirectional locking screws 400 (500, 600, 700, 800), described hereinafter.

Referring to FIG. 4, the body 116 includes four preferably countersunk screw holes 124, 125, 126, 127 for the extension of bone screws 104 therethrough (FIG. 2). One of the screw holes, 127, is preferably generally oval in shape permitting longitudinal movement of the plate 102 relative to the shaft of a bone screw when the screw is not clamped against the plate. The screw holes may be any hole type used for attaching a fixation structure, either threaded or non-threaded, such that a cortical screw or a locking screw may be coupled relative to the plate and underlying bone.

Referring to FIGS. 3 and 4, according to one preferred aspect of the plate 102, the head portion 118 includes a proximal first set of threaded preferably cylindrical threaded holes 134 (for placement of locking screws 106 and/or 108 therein) and a relatively distal second set of threaded preferably cylindrical threaded holes 138 (for placement of locking screw 106 and/or 108 therein). The threaded holes 134 of the first set are arranged substantially parallel to a line $L_1$ that is preferably slightly oblique (e.g., by 5°-10°) relative to a perpendicular to the longitudinal axis of the body portion 116. Axes through the first set of threaded holes are preferably oblique relative to each other, and are preferably angled relative to each other in two dimensions, generally as described in commonly-owned U.S. Pat. No. 6,364,882, which is hereby incorporated by reference herein in its entirety. This orientation of the locking screws operates to stabilize and secure the head 118 of the plate 102 on the bone even where such locking screws 106 do not have threaded shafts.

The second set of threaded holes 138 is provided relatively distal of the first set of threaded holes 134 and is most preferably primarily located in a buttress portion 120 of the plate. Each of the threaded holes 138 preferably defines an axis that is oblique relative to the other of threaded holes 136 and 138. Thus, each and every locking screw 106, 108 when positioned within respective threaded holes 134, 138 defines a distinct axis relative to the other locking screws. Moreover, the axes of the threaded holes 138 are preferably oriented relative to the axes of threaded holes 134 such that locking screws 106, 108 within threaded holes 138 extend (or define axes which extend) between locking screws (or axes thereof) within threaded holes 134 in an interleaved manner.

Locking screws 106 have a threaded head and a non-threaded shaft, and locking screws 108 have both a threaded head and at least a portion of the shaft is threaded. Exemplar locking screws are described in more detail in U.S. Pat. No. 6,364,882, which is hereby incorporated by reference herein in its entirety. Either locking screws 106 or 108, or a combination thereof may be used at the discretion of the surgeon when the surgeon elects to implants unidirectional screws. As discussed in detail below, the surgeon may also opt to implant omnidirectional surgeon-directed screws 400 in place of any of the unidirectional screws 106, 108.

Referring back to FIGS. 3 and 4, axes through the first set of threaded holes 134 (indicated by the locking screws 106 extending therethrough) are preferably oblique relative to each other, and are preferably angled relative to each other in two dimensions, generally as described in commonly-owned U.S. Pat. No. 6,364,882, which is hereby incorporated by reference herein in its entirety. More particularly, the axes of the holes 134 are angled so as to extend through the subchondral bone just below and parallel to the curving articular surface of the distal radius so that, in lateral view, unidirectional locking screws extending through the holes 134 provide support for the dorsal aspect of the subchondral bone. This oblique orientation of the locking screws operates to stabilize the dorsal aspects of the subchondral bone of the articular surface relative to the head 118 of the plate 102 even where such locking screws 106 do not have threaded shafts.

With respect to the distal radius plate described, the lateral and medial threaded holes of the first set of threaded holes 134 are for placement of locking screws intended to extend into the radial styloid and ulnar fragment of the distal radius bone. With respect to such holes it may be desired to angle the locking screws at a surgeon directed angle relative to the hole axis to facilitate the capture of corresponding bone fragments.

The second set of holes 138 is provided relatively distal of the first set of holes 134 and is most preferably primarily located in a tapered supporting buttress portion 120 of the plate. Each of the holes 138 preferably defines an axis that is oblique relative to the other of holes 136 and 138. Thus, each and every locking screw 106, 108 when positioned within respective holes 134, 138 preferably defines a distinct non-parallel axis relative to the other locking screws. Moreover, the axes of the holes 138 are preferably oriented relative to the axes of 134 such that locking screws 106, 108 within holes 138 extend (or define axes which extend) between locking screws (or axes thereof) within holes 134 in an interleaved manner which, in lateral view, defines a cradle that provides support for the central aspect of the subchondral bone of the distal radius. The oblique orientation of the locking screws provides such stabilization even where such locking screws 106 do not have threaded shafts.

Thus, the axes of the holes 134, 138 of the plate are preferably oriented so that unidirectional screws inserted therein will provide the maximum support without necessitating deviation from the predefined axes.

Figure 7:
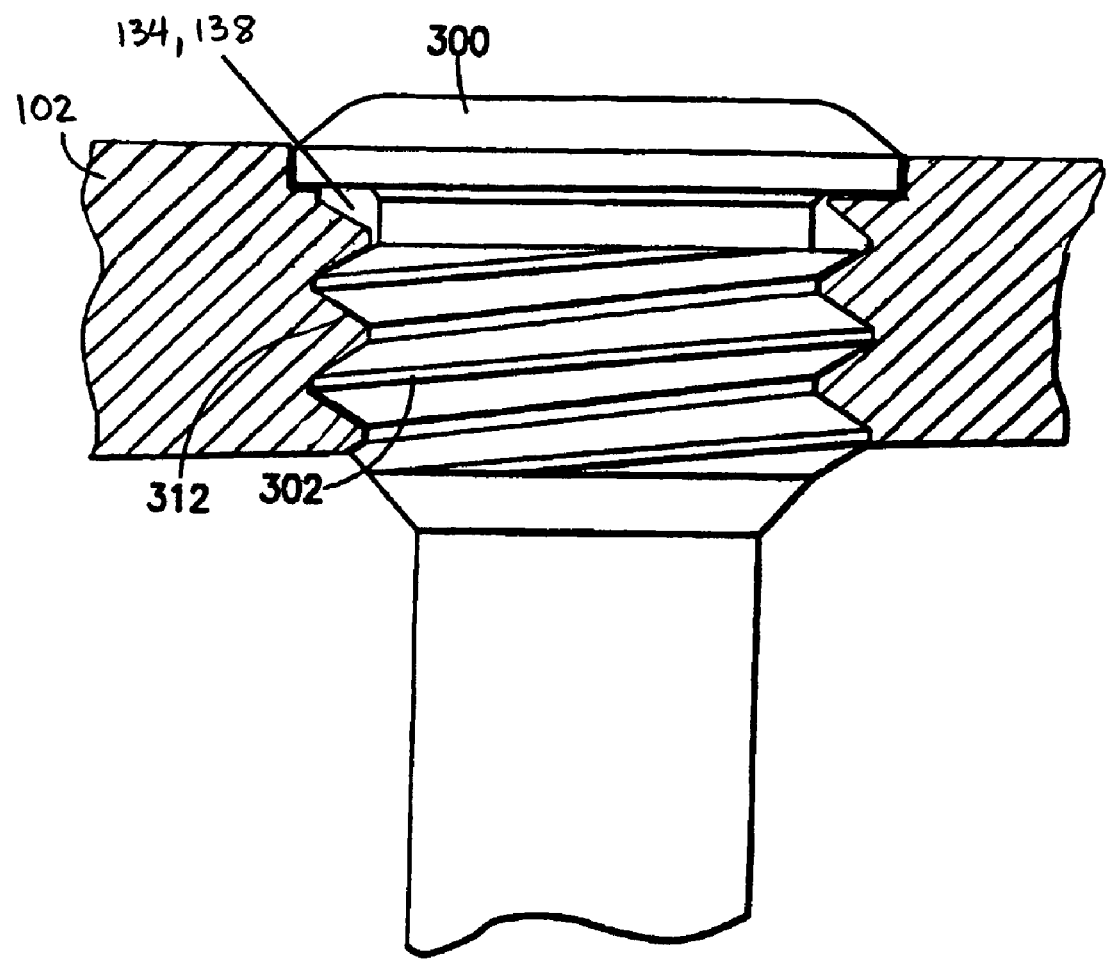
FIG. 7 is a schematic section view of a unidirectional locking screw coupled within a threaded hole.

Referring to FIG. 7, in the embodiment described above, each of the holes 134, 138 of the plate 102 has an internal thread 312 that extends helically along the same characteristic direction (right-hand or left-handed). The internal thread 312 of each screw hole preferably has a cylindrical contour. Each unidirectional locking screw has a head 300 with an external thread 302 that extends helically in the same direction as the internal threads of the locking screw holes 134, 138 of the plate. The threads of the head 300 threadably engage with the preformed threads 312 of a given screw hole. The internal thread 312 and the external thread 302 preferably each have an 'angle of thread' of 60 degrees (as defined below). When secured in a given screw hole of the plate, the unidirectional screw extends from the plate 102 at a fixed angular orientation defined by a central axis through the helical threads of the given screw hole.

However, it is recognized and appreciated that a surgeon may wish to modify the axial approach of one or more of the locking screws based upon personal preference, or based upon the particular anatomical distinctions of a specific fracture, such as displacement of the radial styloid or ulnar fragment.

In view thereof and in accord with the invention, the system 100 also includes the second set of locking screws 400 (FIGS. 8A-8C) that are adapted to self-tap into the holes 134, 138 in a manner that allows the screws to be secured (e.g., fixed and "locked") at an arbitrary surgeon-directed angle with respect to the axis of the given locking screw hole. The angular orientation of the self-tapping locking screw, which can be omnidirectional within a range, is dictated by the axial force applied by the surgeon to the screw while applying a rotational driving force for inserting the screws 400 into the holes 134, 138. The term "self-tap", "self-tapping" and/or "self-tappable" are used herein to denote that the screw 400 is structured such that it is angularly locked into position against the internal thread of the hole by an interference fit and possibly deformation of the mating structures, rather than a conventional threaded engagement of two preformed threads of the same pitch. These self-tapping locking screws are used to stabilize the fractured bone in a manner similar to the unidirectional locking screws described above. In addition, these self-tapping locking screws provide the surgeon with flexibility, ease of use, and operational efficiency in employing either unidirectional locking screw fixation or surgeon-directed fixation within the same hole.

More particularly, the use of self-tapping locking screws permits the surgeon to modify the angle of approach of a fixator relative to the axes of screw holes which are already obliquely oriented relative to each other. Thus, substantially greater range of angular diversity between the screws 400 is possible than in the prior art. For example, where in the prior art the holes are parallel and a ±15° angular variation is permitted at any screw hole, the maximum variation between two screws is 30°. In the present invention, if two screw holes already have axes angled 30° relative to each other, given a ±15° angular variation at any screw hole, the maximum variation between two screws is 60°. Moreover, by directing the various hole axes at generally distinct and generally ideal angles for proper subchondral support, the self-tapping angular variation can be used for "fine-tuning" the angle of the screw, as opposed to gross selection of the angle.

Figure 8B:
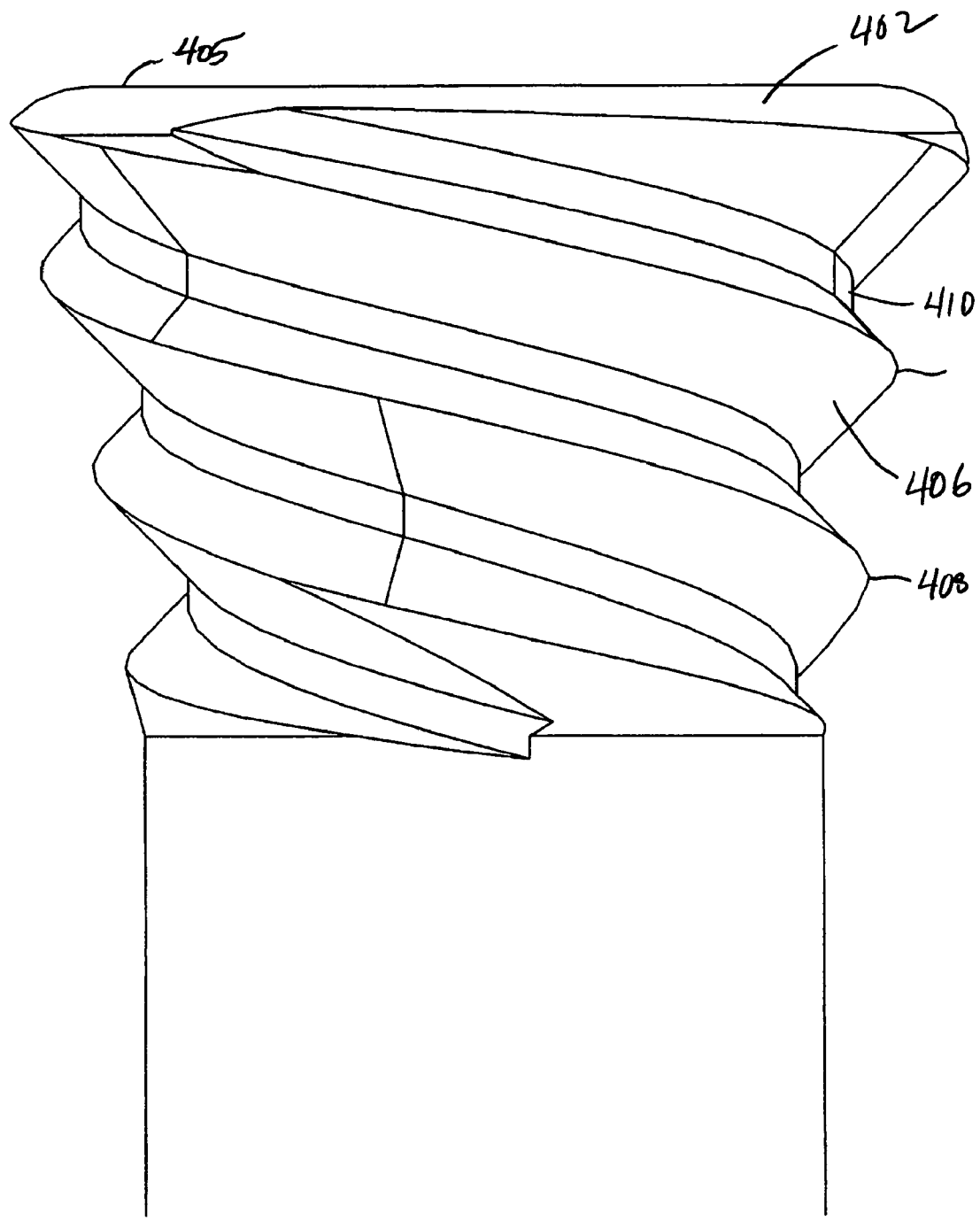
FIG. 8B is a side view of the head of the surgeon directed locking screw of FIG. 8A.

FIGS. 8A-8B illustrate a first embodiment of a self-tapping locking screw 400 in accordance with the present invention. The self-tapping locking screw 400 includes a head 402 and a non-threaded shaft 404. In an alternate embodiment (not shown), the shaft 404 may be threaded (for example, in a manner similar to the shaft of screw 108). The head 402 includes a top surface 405 and an external thread 406. The top surface 405 includes a hole or slot (e.g., a square or hexagonal slot) or other structural feature (not shown) that mates to a driver that is used to forcibly insert and rotate the head 402 of the locking screw 400 into the screw hole to tap new threads. Most preferably, the hole is a square slot, optionally with edge breaks, that provides a substantially larger cross-sectional area (e.g., approximately 40% larger) than in a conventional locking screw of like head size, thereby providing increased surface area for application of higher torque force. The external thread 406 extends helically in the opposite direction relative to the internal threads of the locking screw holes 134, 136 of the plate 102. Thus, external thread 406 is referred to as "reverse-handed" or a "reverse-hand" thread. As best shown in FIG. 8B, the profile of the thread 406 is conical in shape. Such a conical profile may be formed by the crest 408 and root 410 of the thread 406 both having a conical profile wherein the conical profile of the root 410 is offset radially inward and vertically with respect the conical profile of the crest 408. The dimensions of the reverse-hand thread 406 are selected such that the reverse-hand thread 406 self-taps into the internal thread of a screw hole (134, 138) of the plate 102 in a manner that allows the screw 400 to be secured at the directed angle relative to the axis of the given screw hole. In the embodiment shown, the angular orientation of the screw 400 can be set to any angle β from 0 to ±15°.

Figure 8C:
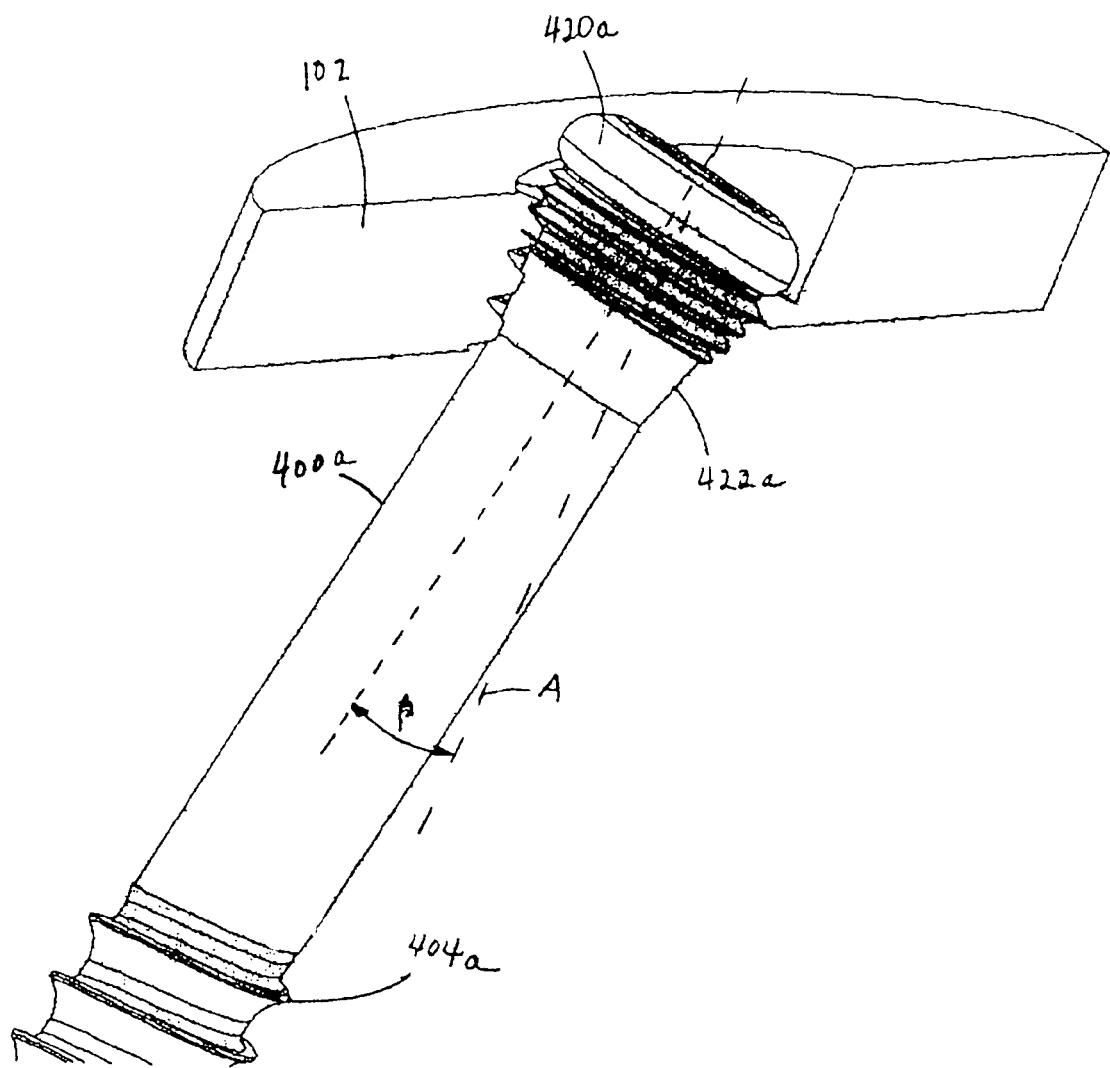
FIG. 8C is a schematic illustration of a surgeon directed locking screw inserted into and securely fixed within a threaded hole of the plate of FIGS. 1-6.

FIG. 8C illustrates another similar self-tapping locking screw 400a secured in place in the plate 102 at an angle β of 10° relative to the axis A of the screw hole. Differences between screws 400 (FIGS. 8A, 8B) and 400a (FIG. 8C) include a non-threaded upper head portion 420a (which functions as a stop to limit how far the screw head can be tapped into the screw hole), a tapered neck 422a between the head and shaft portions, and an at least partially threaded shaft 404a (to lag bone fragments).

The 'angle of thread' is a feature of a thread defined by the angle between adjacent flanks (i.e., the thread surface extending between the crest and root) measured at a cross-section of the thread. The angle of thread of the internal thread of the screw holes (134, 138) and the angle of thread of the reverse-handed external thread 406 of the screw 400 may be equal (or substantially similar) at approximately 60 degrees. These angles may be increased (for example, greater than 70 degrees and more preferably 75 degrees) for improved fixation. In alternate embodiments, these angles may be substantially different from one another.

Moreover, the reverse-handed external thread 406 of the screw 400 may comprise a two-start thread structure. A two-start thread structure is well known and generally includes a double helically thread design with the threads offset by 180°. This structure will overcome wobbling because the external threads on the screw head contact the internal thread of the screw hole on opposite sides of the head 402 with opposing diametric forces as the head 402 enters the threaded screw hole.

Figure 9:
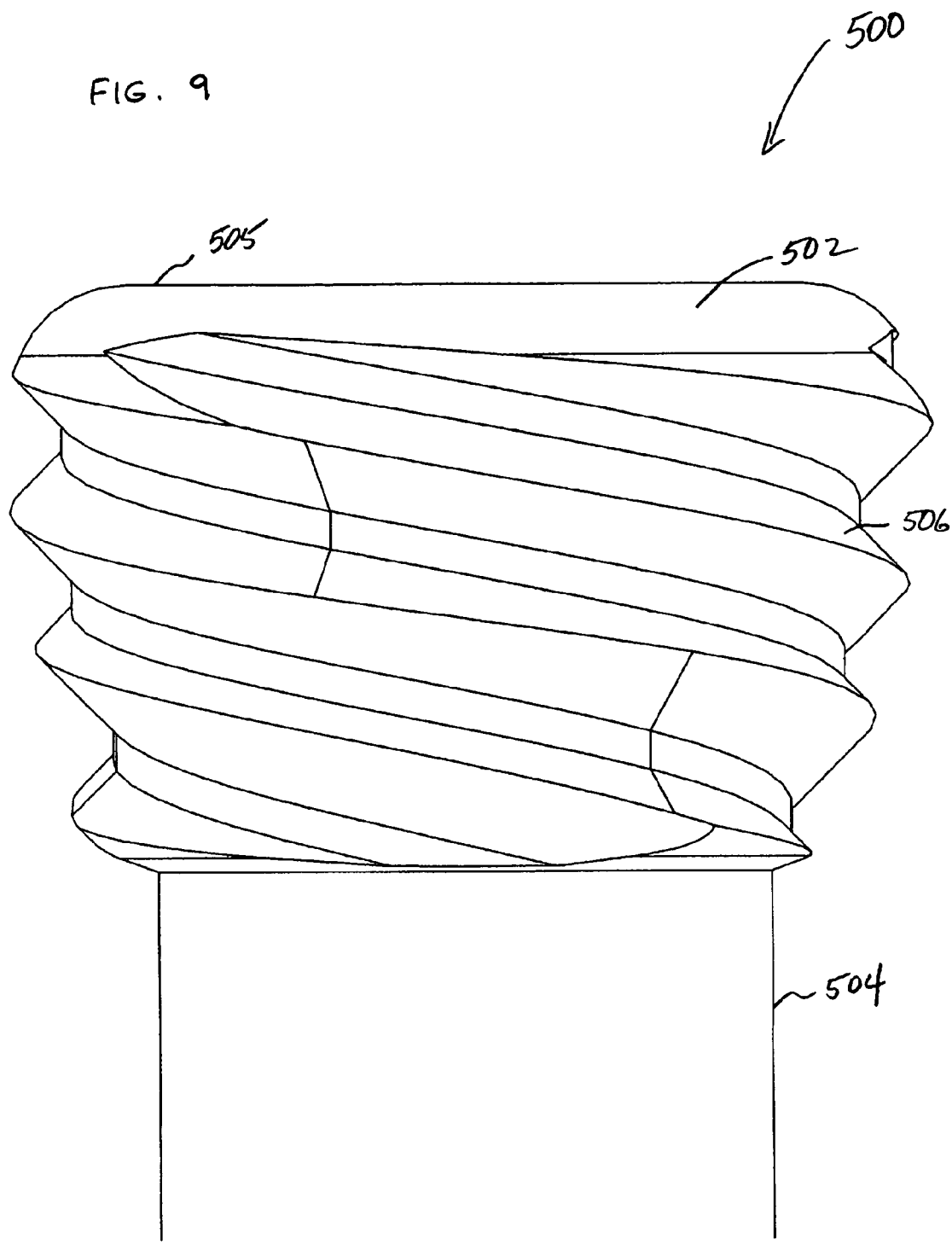
FIG. 9 is a side view of the head of an alternate surgeon directed locking screw in accordance with the present invention.

FIG. 9 illustrates a second embodiment of an omnidirectional locking screw 500 for use through threaded holes in accordance with the present invention. The screw 500 includes a head 502 and a shaft 504 (which may be threaded or non-threaded). The head 502 includes a top surface 505 and an external thread 506. The top surface 505 includes a hole or slot (e.g., a square or hexagonal slot) or other structural feature (not shown) that mates to a driver that is used to forcibly insert and rotate the head 502 of the locking screw 500. The external thread 506 extends helically in the opposite direction relative to the internal threads of the screw holes (134, 138) of the plate 102. The profile of the thread 506 is spherical in shape. The dimensions of the reverse-hand thread 506 are selected such that the reverse-hand thread 506 self-taps into the internal thread of a screw hole (134, 138) of the plate 102 in a manner that allows the screw 500 to be secured (e.g., fixed) at an arbitrary angle within a range with respect to the axis of the given screw hole. The angle of thread of the internal thread of the screw holes (134, 138) and the angle of thread of the reverse-handed external thread 506 may be equal (or substantially similar) at an angle greater than 55 degrees, for example 60 degrees. These angles may be increased (for example, greater than 70 degrees and more preferably 75 degrees) for improved fixation. In alternate embodiments, these angles may be substantially different from one another. Moreover, the reverse-handed external thread 506 of the self-tapping locking screw 500 may comprise a two-start thread structure, as described above. This structure will overcome wobbling because the screw head applies contacts to the internal thread of the screw hole on opposite sides of the head 502 with opposing diametric forces as the head 502 enters the screw hole.

Note that the spherical profile of the thread 506 of the locking screw 500 provides a longer length of engagement that the conical profile of the thread 406 of the screw 400. However, the conical profile locks quicker than the spherical profile.

Figure 10:
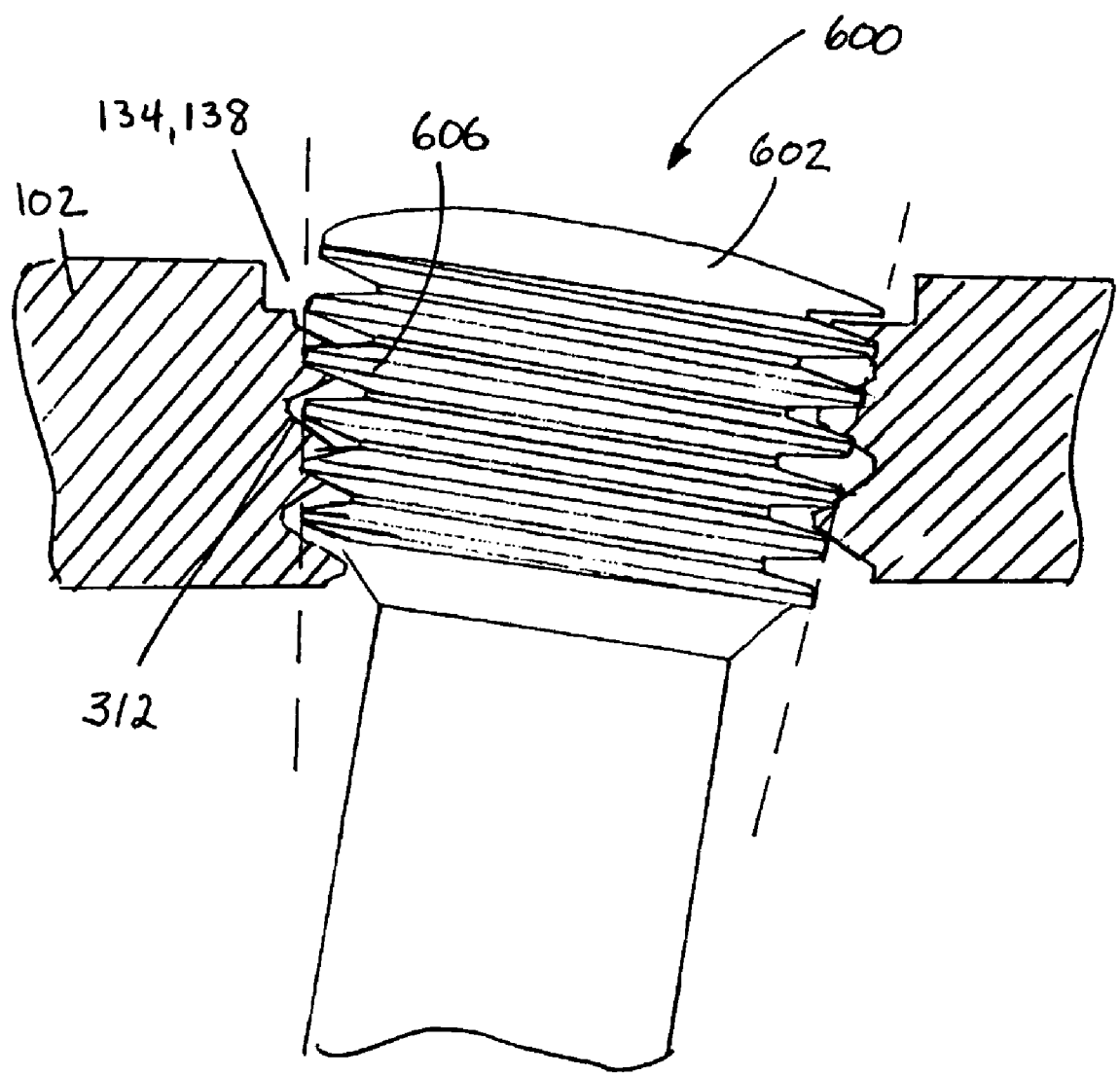
FIG. 10 is a section view of second embodiment of a surgeon directed locking screw coupled within a threaded hole according to the invention.

Turning now to FIG. 10, another embodiment of a surgeon directed locking screw system according to the invention is shown. The self-tapping external structure of the head of each surgeon-directed screw of the first set is realized by external threads 606 that runs in the same direction as the internal threads 312 of the threaded holes 134, 138 of the plate 102; for example, right-hand external threads on the screw head for insertion through a right-hand threaded screw hole. Such external and internal threads are preferably, though not necessarily of significantly different pitch from each other. If of a different pitch, the threads purposefully cross-thread providing an interference fit. The external threads 606 may have a lesser angle of attack against the plate threads than the reverse thread screws. In fact, the external and internal threads 606, 312 can be in the same and even have the same pitch and be made to cross thread by virtue of the angle of insertion. The head 602 of the screw 600 preferably has a conical (as indicated by broken lines) or spherical profile.

Figure 11:
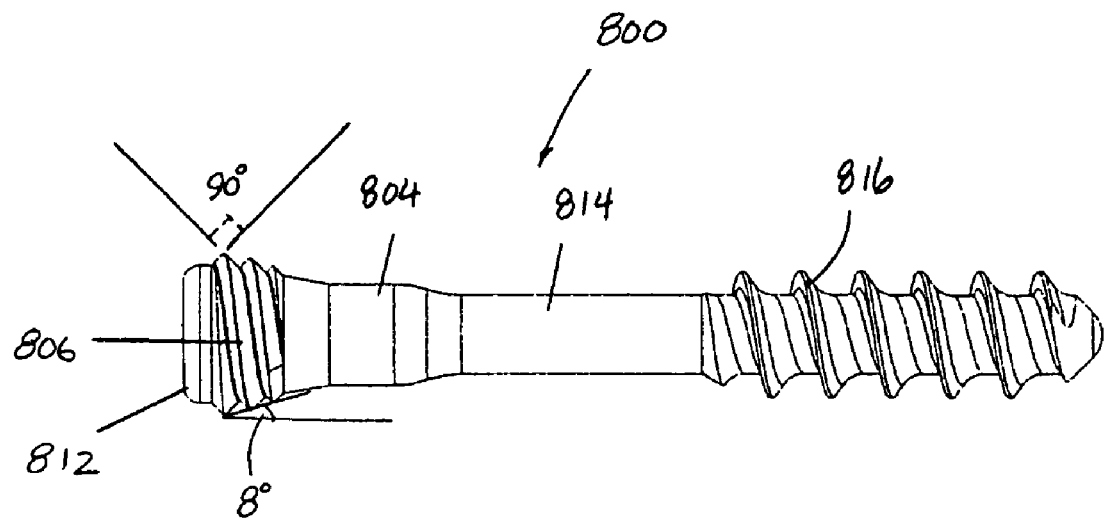
FIG. 11 is a side elevation of another embodiment of a surgeon directed locking screw according to the invention.
Figure 12:
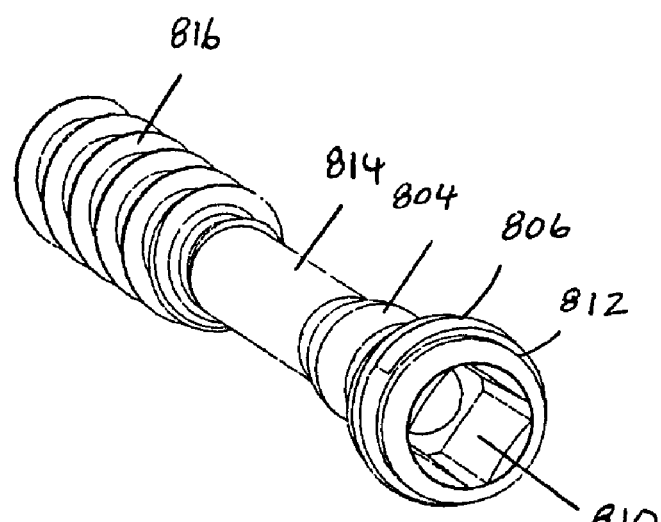
FIG. 12 is a perspective view of the locking screw of FIG. 11.

In order to aid insertion (in any threaded screw embodiment, but) particularly where the threads of the screw head and the screw hole are wound in the same direction, it is desirable that the threads of the screw head be made of a harder material than the internal threads of the screw hole, and preferably the locking screw is made of a harder metal (metal alloy) than the bone plate. Referring to FIGS. 11 and 12, with that in mind, an exemplar preferred screw 800 is shown. Locking screw 800 is made of a cobalt chrome (CoCr) alloy, e.g., Co-28Cr-6 Mb for insertion into a plate made of titanium alloy, e.g., Ti-6Al-4V. In an exemplar embodiment suitable for use in subchondral support with a plate intended for volar placement to stabilize a distal radius fracture, the locking screw 800 includes a head 800 that is 2.5 mm in diameter, that is tapered by 8°, that has threads 806 with an angle of thread at 90° (for internal threads with angle of thread at 60°), and that has two-start threads at 180° apart. The larger angle of thread requires more torque to insert the screw. Therefore, the driver slot 810 at the rear of the head 802 is a relatively larger square slot facilitating a relatively larger manual application of torque to the locking screw and the stability of the locking screw on the driver. The large slot is possible because of the increased strength of the CoCr alloy (ultimate strength 203,000 ksi) relative to the conventional unidirectional screw material of Ti alloy (ultimate strength 138,000 ksi). The approximately 50% increase in strength permits the area of the head surrounding the square slot to be approximately 20-30% thinner and maintain at least the same strength as a conventional unidirectional screw. These features facilitate driving the locking screw at an angle relative to the hole axis and fixing it therein. For example, the tapered head achieves directional mobility during insertion and permits three complete turns of threads to be located on the head (as opposed to two turns for a conventional locking screw), the large angle of thread removes more material from the thread hole providing more interference between the screw and hole, the two-start thread provides stability during non-axial insertion, and the driver slot allows sufficiently larger force to be applied to the locking screw. By way of example, using the relatively larger square slot enables a comfortable manual application of 5-7 in/lb to the locking screw (in distinction from 2-3 in/lb with a smaller conventional square slot). In addition, the proximal portion 812 of the head is rounded and less than 1 mm protrudes above the plate when fully inserted, thus providing an atraumatic profile to the surrounding soft tissue when in use.

It is recognized that the CoCr alloy is significantly stronger, harder, and stiffer than titanium alloy. As such, it is also an aspect of the invention to provide a locking screw that while made of a substantially harder and stiffer material has a similar flexibility to a standard unidirectional locking screw so as to permit the surgeon direction self-tapping and unidirectional locking screws to share load equally within the fracture and as part of the fracture support system. To that end, a portion 814 of the shaft 804 of locking screw is reduced in diameter. The shaft is preferably reduced in accord with the equation for deflection of a beam with point load to which the beams (screws) are subject at the ends:

$$Y_{max} = \frac{FL^3}{3EI}$$

where Y is the deflection of the beam, F is the load applied at the end of the beam and L is the length of the beam, E is the modulus of the material, and I is the second moment of area of beam.

Setting this equation equal to itself and varying the material, provides:

$$\frac{FL^3}{3E_{CoCr}I} = \frac{FL^3}{3E_{Ti6Al4V}I},$$

where I is the second moment of area and for a round beam equals $\pi d^4/64$. The equation is then simplified by eliminating all of the variables that are common on both sides. The result is:

$$\frac{1}{E_{CoCr}D_{CoCr}^4} = \frac{1}{E_{Ti6Al4V}D_{Ti6Al4V}^4},$$

where E is know for both materials, the diameter D is known for the conventional unidirectional screws, and the reduced D for the CoCr alloy is then solved. Once the reduced diameter of the CoCr alloy surgeon directed screw is solved, it is preferred that the value be slightly decreased in the manufactured surgeon directed screw to ensure that in no event does the surgeon directed screw give up its purchase in the plate before bending.

In a preferred example, the shaft of the screw is reduced from 0.078 inch to 0.064 inch to substantially mimic the flexibility of the titanium unidirectional locking screws when loaded axially. It is preferable that such reduction 814 occur spaced below the threads 806 of the head 802 (e.g., preferably at least 2 mm below), so that relatively adjacent the plate the shaft 804 of surgeon-directed locking screw is well-adapted to transfer shear loads to the plate, and spaced upwards from any threads on the shaft. The distal end of the shaft may be provided with threads 816 for lag functionality. As such, the pitch of such threads is preferably substantially the same as the pitch of threads 806.

Figure 13A:
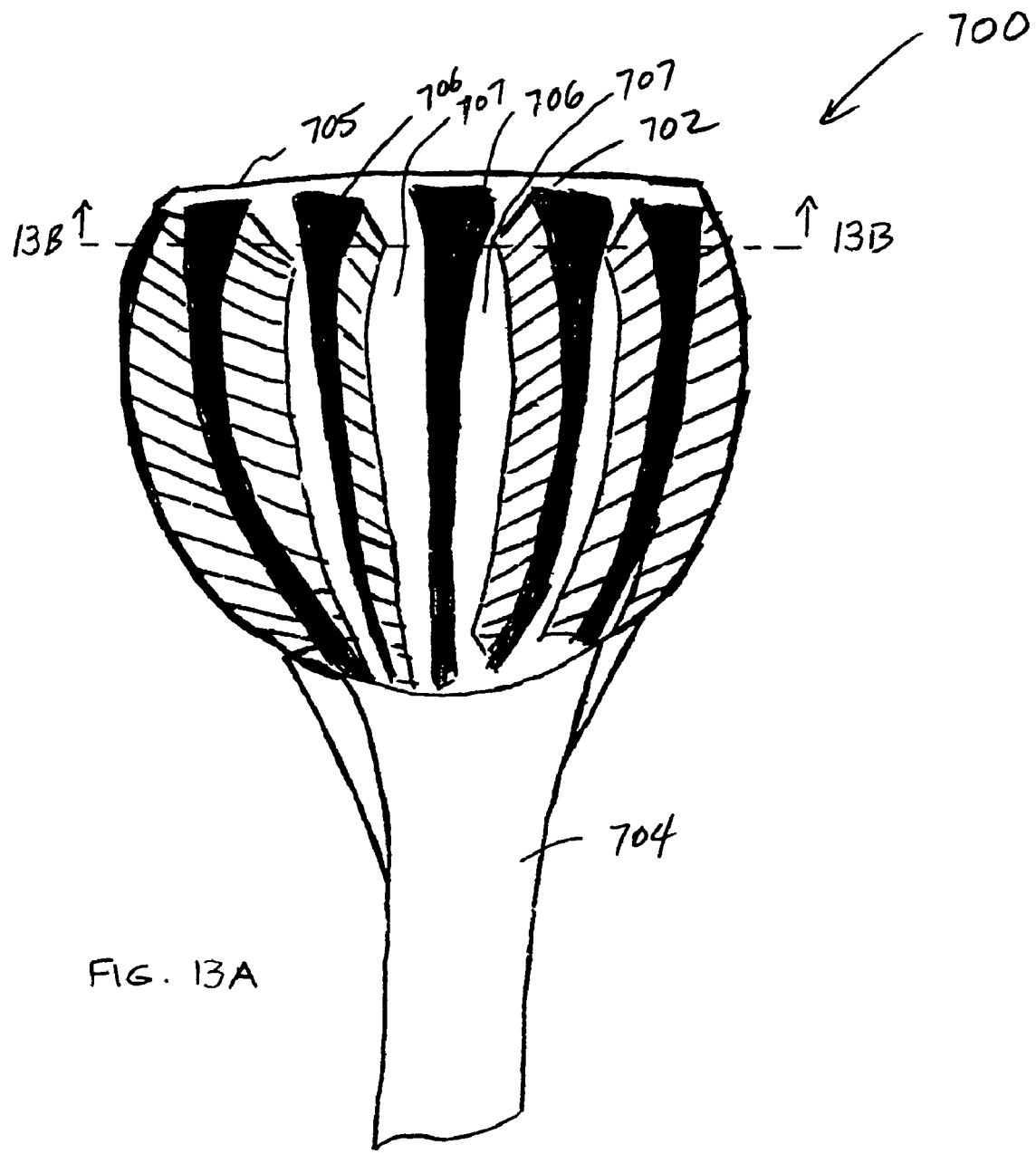
FIG. 13A is a side view of the head of an embodiment surgeon directed locking screw in accordance with the present invention.
Figure 13B:
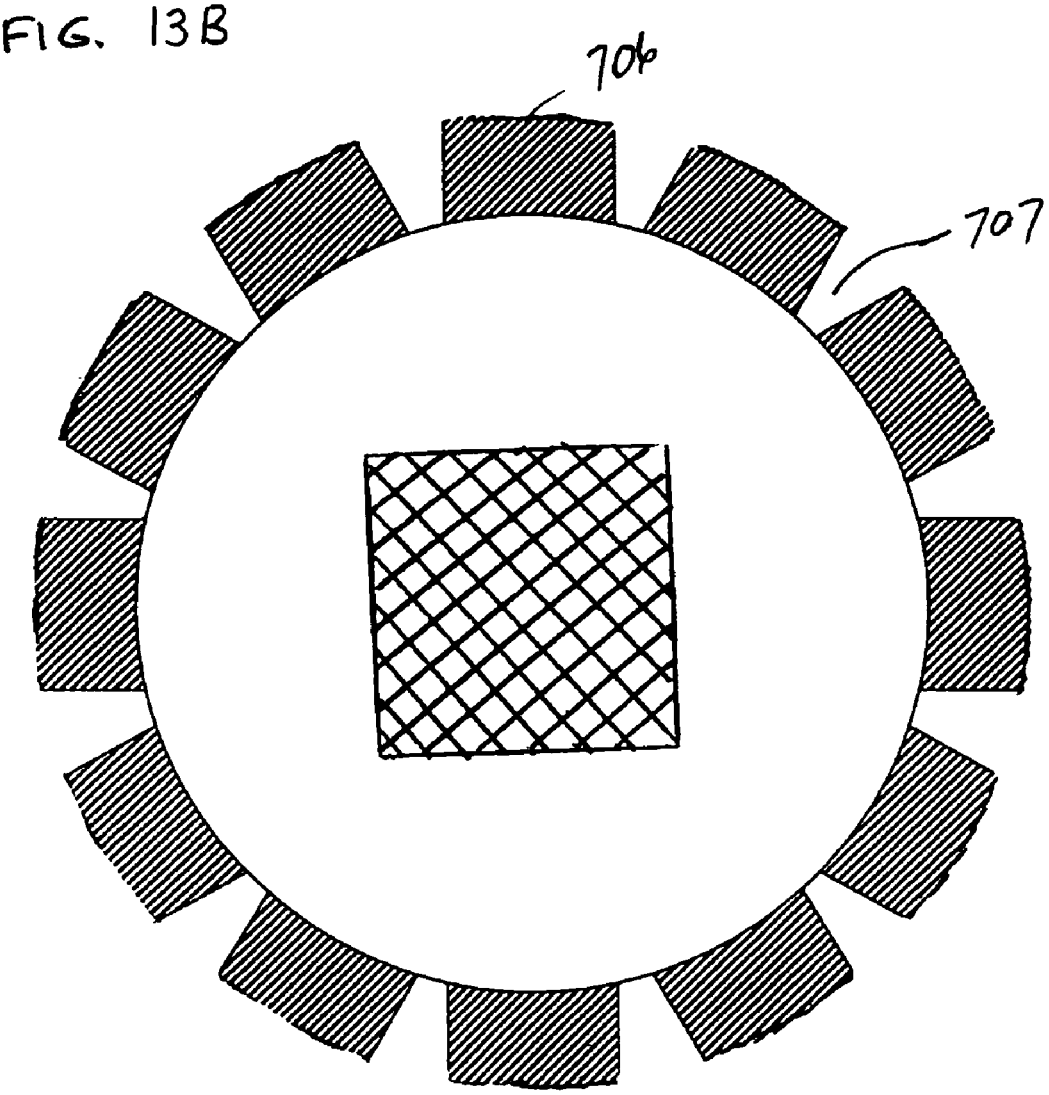
FIG. 13B is a cross-sectional view through the head of the surgeon directed locking screw of FIG. 13A.

FIGS. 13A and 13B illustrate a fourth embodiment of an omnidirectional screw 700 in accordance with the present invention. The screw 700 includes a head 702 and a shaft 704 (which may be threaded or non-threaded). The head 702 includes a top surface 705 and a set of external ridges 706 and external grooves 707 that are radially spaced apart from one another about the outer circumference of the head 702 and that extend in vertical directions substantially parallel to the central axis of the screw 700 as shown. The profile of the ridges 705 is preferably spherical in shape as shown; however, a conical profile or other suitable profile may be used. The dimensions of the ridges 705 and grooves 706 are selected such that the ridges 705 are deformed by the internal thread of a screw hole (134, 138) of the plate 702 in a manner that allows the screw 700 to be secured at an arbitrary angle within a range with respect to the axis of the given screw hole. Similar to the operation of the screw 400 of FIGS. 8A-8B, the angular orientation of the screw 700 is dictated by the axial direction of the insertion force applied to the head 702 by the surgeon during forcible insertion and rotation of the head 702 during the surgical operation.

The cross-section of FIG. 13B shows the ridges 706 and grooves 707 spaced apart from one another about the outer circumference of the head 702. It also shows a square hole 708 that mates to a driver that is used to forcibly insert and rotate the head 702 of the locking screw 700. The ridges 706 may have a variable width along their extent in the vertical direction with their greatest width at top and narrowest width near the bottom of the head 702 as shown in FIG. 13A. Alternatively, the ridges 706 may have a constant width along their extent in the vertical direction.

In order to facilitate the self-tapping feature of the self-tapping locking screw described herein, the material of the external contact structure (e.g., reverse-handed external thread, same hand external thread of same or dissimilar pitch, or external ridges) of the self-tapping locking screw may be harder than the material of the internal threads of the locking screw holes of the plate, as described above with respect to one exemplar embodiment wherein the locking screw is made of CoCr alloy and the plate is made of Ti alloy. Other metal or metal alloy combinations of harder and softer metals can also be used. By way of another example, the internal threads of the locking screw holes may be non-anodized while the external contact structures of the locking screw are anodized, but otherwise of the same material. Such non-anodized internal threads may be realized by anodizing the plate 102 before drilling and tapping the threads of the screw holes therein. In other embodiments where the internal threads of the screw holes deform the head of the screw to secure the screw, the screw hole internal thread is preferably harder than the structure (e.g., ridges) on the screw head which are intended to be deformed. Alternatively, the external contact structure cut into the plate because of geometrical configurations of the threads. For example, the internal plate threads can be made relatively weaker than the screw threads by providing a relatively more acute cross section apical angle to the internal threads than the peg threads. Furthermore, the external screw threads can be trapezoidal in cross section providing greater strength by geometrical means in addition to or as opposed to being made of a harder material.

For the omnidirectional self-tapping screws described herein, the top part of head of the screws are preferably wider than the width of the threaded screw holes 134, 138 of the plate 102 to ensure that the heads of the screws bottom out against the surface of the plate 102 (i.e., to prevent the omnidirectional screws from being inserted completely through the threaded screw hole).

These omnidirectional self-tapping locking screws described herein are used to stabilize a fractured bone in a manner similar to the unidirectional locking screws described above. Advantageously, the same holes in the fixation plate (without modification or reconfiguration) can support both unidirectional or omnidirectional screws. Thus, the surgeon is afforded flexibility, ease of use, and operational efficiency. Moreover, the omnidirectional self-tapping screws described herein are inexpensive to manufacture and provide for effective fixation at minimal costs.

While certain unidirectional locking screws (i.e., locking screws that are fixed in respective screw holes 134, 138 only in a single direction that is coaxial with the axis defined by the respective locking screw holes) as well as self-tapping omnidirectional screws have been disclosed for use in the threaded holes of the plate, it is appreciated that other locking screw systems, such as that disclosed in co-owned U.S. Pat. No. 6,440,135 or co-owned U.S. Pat. No. 6,767,351, both of which are hereby incorporated by reference herein in their entireties, may also be used in conjunction with the plate 102. In such locking screw systems, the locking screw holes and locking screw are structurally adapted such that individual locking screw may be fixed at any angle within a range of angles. In addition, while less preferable, one or both sets of the locking screw may be replaced by preferably blunt tines which are integrated into the plate such that the plate and tines are unitary in construct. Similarly, other elongate projections may be coupled to the plate to define the desired support.

The system may also include K-wires 110, and K-wire alignment holes 140, 152a, 152b, 152c, 154 in the plate 102 (FIGS. 1-6). The use of K-wires 110 through K-wire alignment holes and the advantage thereof is described in detail in co-owned U.S. Ser. No. 10/689,797, filed Oct. 21, 2003, which is incorporated herein in its entirety.

There have been described and illustrated herein embodiments of a bone fixation plate, and particularly plates for fixation of distal radius fractures, as well as a method of aligning and stabilizing a bone fracture and performing an osteotomy. While particular embodiments of the invention have been described, it is not intended that the invention be limited thereto, as it is intended that the invention be as broad in scope as the art will allow and that the specification be read likewise. Thus, while particular preferred materials, dimensions, and relative angles for particular elements of the system have been disclosed, it will be appreciated that other materials, dimensions, and relative angles may be used as well. Further, plates having shapes other than a 'T' may also be used, such as straight plates, lateral and medial columns (generally 'L'-shaped), flared head plates, forked plates, etc. In addition, while a particular number of screw holes, locking screw holes and k-wire holes in the fixation plate have been described, it will be understood another number of holes may be provided in the plate, preferably such that at least two threaded screw holes preferably having axes angled in two dimensions relative to each other are provided. Moreover, while the fixation plate system of the present invention utilizes cylindrical locking screw holes that are compatible with both the threaded head interface for unidirectional locking screw as well as the reverse-hand threaded, same-hand threaded, or ridged head interface for omnidirectional locking screw, it will be appreciated that the invention can be readily extended to incorporate other compatible interface mechanisms. Similarly, different thread designs, such as double or triple threads, can be used for the locking threads of the locking screw holes, unidirectional locking screw and the omnidirectional locking screw. It will therefore be appreciated by those skilled in the art that yet other modifications could be made to the provided invention without deviating from its spirit and scope.

What is claimed is:

1. A bone fixation system, comprising:
a) a titanium bone plate having at least two screw holes, each provided with an internal thread defining a screw hole axis;
b) a cobalt chrome screw having a head and a shaft,
said head tapered and including external two-start threads starting 180° apart, and
said shaft has a first outer diameter with a reduced portion with a smaller second outer diameter that is spaced apart from and located between both said head and an opposite end of said screw,
wherein said cobalt chrome screw can self-tap into said internal thread at an oblique angle relative to the screw hole axis to secure said cobalt chrome screw to said bone plate; and
c) a titanium screw having a head a shaft, said head having threads that threadably engage with the internal thread so that the titanium screw secures to the bone plate along the axis of the screw hole axis to secure said titanium screw to said bone plate, said shaft of said titanium screw has a third outer diameter,
wherein the second and third outer diameters are selected such that the cobalt chrome screw can carry a load no greater than the titanium screw.

2. A bone fixation system, comprising:
a) a titanium bone plate having at least two screw holes, each provided with an internal thread defining a screw hole axis;
b) a titanium screw having a head a shaft, said head having threads that threadably engage with the internal thread so that the titanium screw secures to the bone plate along the axis of the screw hole axis to secure said titanium screw to said bone plate, said shaft of said titanium screw having a first minimum diameter; and
c) a cobalt chrome screw having a head and a shaft,
said head tapered and including external two-start threads starting 180° apart, and
said shaft having a second minimum diameter spaced apart from and located between both said head and an opposite end of said screw,
wherein said cobalt chrome screw can self-tap into said internal thread at an oblique angle relative to the screw hole axis to secure said cobalt chrome screw to said bone plate,
wherein the second diameter is selected relative to said first diameter such that the cobalt chrome screw can carry a load no greater than the titanium screw.

3. A bone fixation assembly, comprising:
a) a bone plate having at least two like screw holes of a common diameter, each provided with an internal thread defining a screw hole axis;
b) a first bone screw made of a first material and having a head a shaft, said head having threads and being threadably engaged with the internal thread of one of said screw holes so that the first bone screw is secured to the bone plate along one of the screw hole axes, said shaft of said first bone screw having a first minimum diameter; and
c) a second bone screw made of a harder second material and having a head and a shaft, said shaft having a second minimum diameter spaced apart from and located between both said head and an opposite end of said screw, said head having an external thread structured to self-tap a thread into said screw holes, said external thread non-mating with said internal thread, wherein said head of said second bone screw is self-tapped through said internal thread at an oblique angle relative to the screw hole axis so as to form a threaded engagement with said bone plate distinct from a threaded engagement with the screw hole threads to secure said second screw to said bone plate, wherein the second diameter is selected relative to said first diameter so that when a load is applied to the end of the shaft of the second bone screw, the second bone screw has a similar flexibility to the first bone screw when a load is applied to distal ends of each of the first and second bone screws.

4. A bone fixation assembly according to claim 3, wherein said first bone screw is made of titanium.

5. A bone fixation assembly according to claim 3, wherein: said second bone screw is made of cobalt chrome.

6. A bone fixation assembly according to claim 5, wherein: said first bone screw is made of titanium.

7. A bone fixation assembly according to claim 6, wherein: said plate is made of titanium.

8. A bone fixation assembly according to claim 3, wherein: said head of said second bone screw is tapered and includes external two-start threads starting 180° apart.

* * * * *